US009433777B2

(12) United States Patent
Zimmerling et al.

(10) Patent No.: US 9,433,777 B2
(45) Date of Patent: *Sep. 6, 2016

(54) IMPACT PROTECTION FOR IMPLANTABLE ELECTRIC LEAD

(71) Applicant: MED-EL Elektromedizinische Geraete GmbH, Innsbruck (AT)

(72) Inventors: Martin Zimmerling, Patsch (AT); Fabrice Béal, Mutters (AT); Davide De Luca, Innsbruck (AT); Dominik Hammerer, Innsbruck (AT); Stefan Hofer, Innsbruck (AT); Philipp Schindler, Aldrans (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,118

(22) Filed: Aug. 3, 2015

(65) Prior Publication Data
US 2015/0335880 A1 Nov. 26, 2015

Related U.S. Application Data

(62) Division of application No. 14/163,002, filed on Jan. 24, 2014, now Pat. No. 9,174,039.

(60) Provisional application No. 61/756,502, filed on Jan. 25, 2013.

(51) Int. Cl.
*A61N 1/00* (2006.01)
*A61N 1/05* (2006.01)

(52) U.S. Cl.
CPC .................. *A61N 1/0541* (2013.01)

(58) Field of Classification Search
CPC ...................................................... A61N 1/054
See application file for complete search history.

(56) References Cited

U.S. PATENT DOCUMENTS

| 5,630,839 A | 5/1997 | Corbett, III et al. .......... 607/137 |
| 5,702,437 A | 12/1997 | Baudino ....................... 607/166 |
| 8,560,084 B2 | 10/2013 | Geroy et al. .................. 607/116 |
| 2004/0055776 A1* | 3/2004 | Milijasevic .............. A61N 1/05 174/108 |

(Continued)

FOREIGN PATENT DOCUMENTS

WO   WO 2012/154256 A1   11/2012   ............... A61N 1/05

OTHER PUBLICATIONS

International Searching Authority, International Search Report and Written Opinion—PCT/US2014/012888, date of mailing Apr. 14, 2014, 22 pages.

(Continued)

*Primary Examiner* — Robert N Wieland
(74) *Attorney, Agent, or Firm* — Sunstein Kann Murphy & Timbers LLP

(57) ABSTRACT

An implantable electric lead arrangement for a medical implant system includes an implantable electric lead with parallel lead wires wound in an elongated helix about a central longitudinal axis. A conical shape lead core is fixed and enclosed within the wire helix for providing impact strain relief to the electric lead by resisting radial and/or axial deformation from external impact force. The conical shape of the lead core is configured for a smooth transition between a lead core portion of the electric lead that is protected against external impact force and a non-lead core portion of the electric lead that is unprotected from external impact force.

8 Claims, 3 Drawing Sheets

(56) References Cited

U.S. PATENT DOCUMENTS

| | | | |
|---|---|---|---|
| 2004/0172116 A1 | 9/2004 | Seifert et al. | 607/119 |
| 2006/0089697 A1* | 4/2006 | Cross, Jr. | A61N 1/056 607/122 |
| 2006/0206185 A1 | 9/2006 | Schuller | 607/137 |
| 2010/0114282 A1 | 5/2010 | Ebert et al. | 607/116 |
| 2010/0179630 A1 | 7/2010 | Williams | 607/127 |
| 2010/0204767 A1 | 8/2010 | Zhao | 607/122 |
| 2010/0305676 A1 | 12/2010 | Dadd et al. | 607/137 |
| 2011/0288388 A1 | 11/2011 | Shah et al. | 600/347 |
| 2011/0295352 A1 | 12/2011 | Thenuwara et al. | 607/137 |
| 2012/0004715 A1 | 1/2012 | Ramachandran et al. | 607/137 |
| 2012/0078339 A1 | 3/2012 | Schuller | 607/148 |
| 2012/0101559 A1 | 4/2012 | Jolly et al. | 607/137 |
| 2014/0296954 A1 | 10/2014 | Wells | 607/116 |

OTHER PUBLICATIONS

International Searching Authority, International Search Report and Written Opinion—PCT/US2014/012632, date of mailing Mar. 25, 2014, 14 pages.

\* cited by examiner

IMPACT PROTECTION FOR IMPLANTABLE ELECTRIC LEAD

This application is a divisional of co-pending U.S. patent application Ser. No. 14/163,002, filed Jan. 24, 2014, now U.S. Pat. No. 9,174,039, issued Nov. 3, 2015, which in turn claims priority from U.S. Provisional Patent Application 61/756,502, filed Jan. 25, 2013, both of which are incorporated herein by reference in their entireties.

FIELD OF THE INVENTION

The present invention relates to medical implants, and more specifically to an implantable electrode arrangement used in medical implant systems such as middle ear implants (MEI), cochlear implants (CI) and vestibular implants (VI).

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple lead wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth.

U.S. Patent Publication 2010/0305676 ("Dadd," incorporated herein by reference) describes winding the lead wires in the extra-cochlear segment of the electrode lead in a helical shape to make that portion of the electrode lead stronger. Dadd is quite clear that such a helical portion does not extend into the intra-cochlear electrode array which needs to be much more flexible than the extra-cochlear lead in order to minimize trauma to the cochlear tissues when the array is inserted.

U.S. Patent Publication 2010/0204768 ("Jolly," incorporated herein by reference) describes winding the individual lead wires in the intra-cochlear electrode array in an elongated helical shape where each wire is separate and independent.

Electrode leads of active implantable medical devices including Middle Ear Implants (MEI's), Cochlear Implants (CI's), Brainstem Implants (BI's) and Vestibular Implants (VI's) need to be small in diameter but also they carry multiple lead wires. Electrode leads also need to be robust against external mechanical impacts, especially in locations where the electrode lead is placed on top of the skull bone only covered by the skin. In case of a mechanical impact on an unprotected electrode lead, the elastic silicone electrode carrier material is compressed and the electrode lead becomes temporarily locally thinner and elongated. Lead wires at the affected location experience local tensile forces and can even break. This is also the case for helically formed wires within a silicone electrode carrier since they are forced to expand nearly the same amount as the carrier material itself.

To deal with this problem, some implant designs arrange for the electrode lead to exits the implantable processor housing so that the electrode lead never lies superficially on top of bone. One disadvantage of such designs in the case of cochlear implants is that the implant housing must be placed in a very exactly defined position relative to the ear. For implant designs where the electrode lead emerges from the side of the implant housing, the surgeon is recommended to drill an electrode channel into the bone, which is time consuming so that not every surgeon follows the recommendations. Some electrode lead design include a rigid impact protector that surrounds the electrode lead, but that approach reduces the flexibility of the electrode lead which in turn makes the surgical implantation procedure more difficult. And in case of a mechanical impact in the area of the electrode lead, a rigid impact protector may protect the electrode from damage but also may cause trauma in the surrounding tissue when it is pressed against the protector.

SUMMARY OF THE INVENTION

Embodiments of the present invention are directed to an implantable electric lead arrangement for a medical implant system that includes an implantable electric lead with parallel lead wires wound in an elongated helix about a central longitudinal axis. A conical shape lead core is fixed and enclosed within the wire helix for providing impact strain relief to the electric lead by resisting radial and/or axial deformation from external impact force. The conical shape of the lead core is configured for a smooth transition between a lead core portion of the electric lead that is protected against external impact force and a non-lead core portion of the electric lead that is unprotected from external impact force.

The lead core may be made of a flexible polymer material, which may have an elastic module value and/or a shore-A hardness value greater than some given threshold value. Or the lead core may be made of a flexible metallic material. There may be support ribs perpendicular to the lead core that are distributed along the length of the lead core. A base end of the lead core may have a diameter less than 0.7 times the diameter of the electric lead. The electric lead specifically may be a cochlear implant electrode lead that is connected at one end to an implantable cochlear implant processor and connected at another end to an intracochlear electrode array.

DETAILED DESCRIPTION OF SPECIFIC EMBODIMENTS

Figure 1:
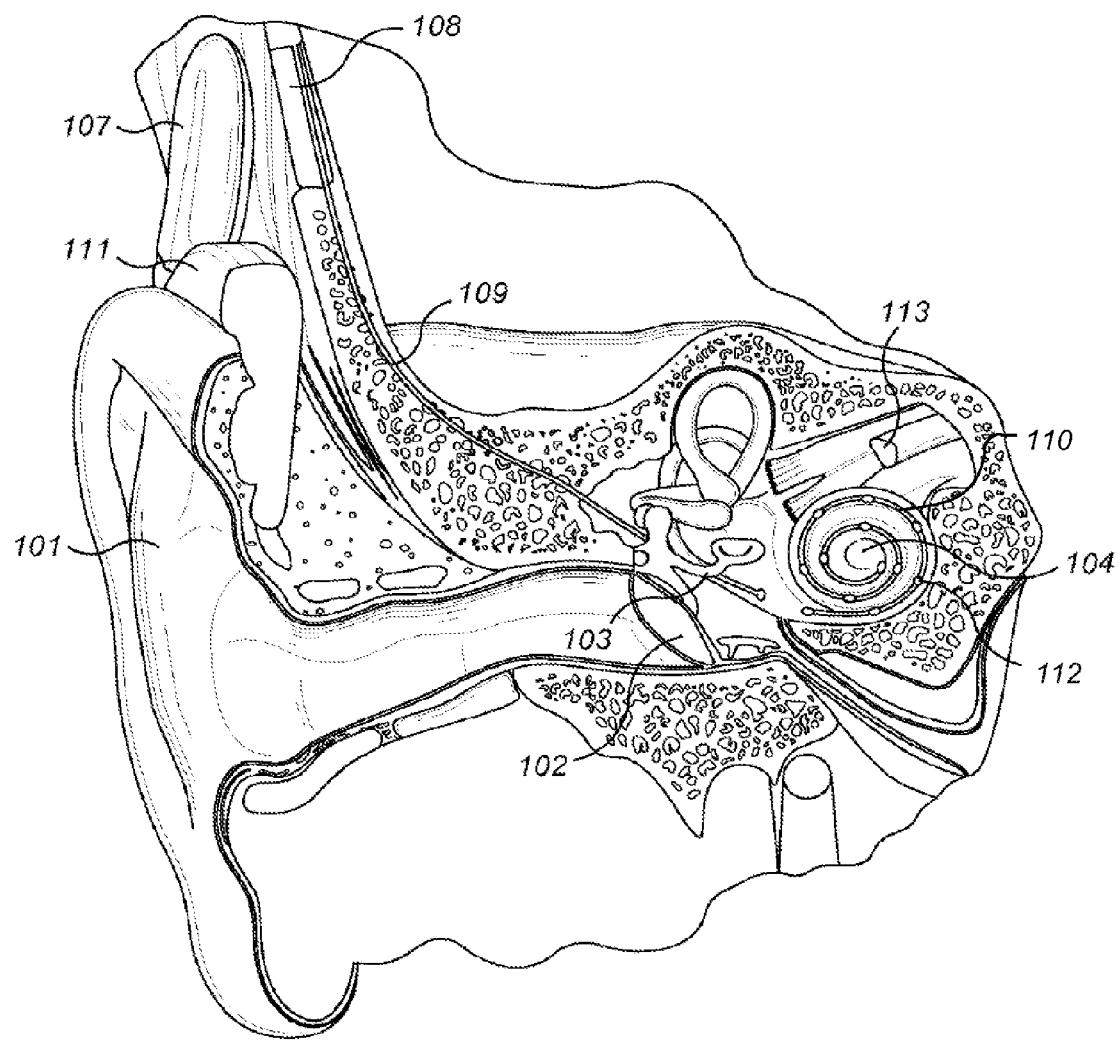
FIG. 1 shows anatomical structures in a human ear having a cochlear implant system.
Figure 2:
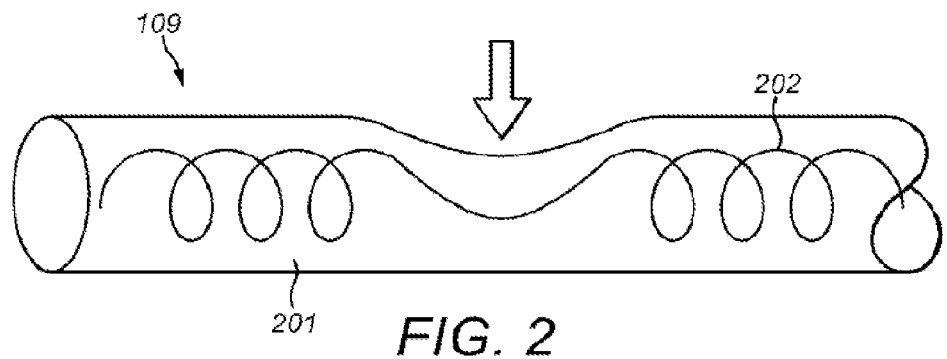
FIG. 2 shows the local effect of a mechanical impact force on a portion of an implantable electric lead.

FIG. 2 shows how longitudinal deformation of a cochlear implant electrode lead 109 occurs in response to radial and/or axial deformation caused by an external impact or exerted pressure onto the electrode lead 109 which thins and elongates the resilient material of the lead carrier 201 and creates a local tensile force on the lead wires 202. Such longitudinal deformation should be prevented or strongly suppressed. Reduced longitudinal deformation as a response to radially induced deformation is especially a challenge in electric leads 109 having helically wound lead wires 202 as in FIG. 2. Embodiments of the present invention are directed to an implantable electric lead, for example, a cochlear implant electric lead 109, which is more robust against radial and/or axial deformation to avoid wire breakage within the electric lead 109. This most often occurs relatively close to the stimulator housing where after implantation the electric lead 109 runs on top of the skull bone.

Figure 3:
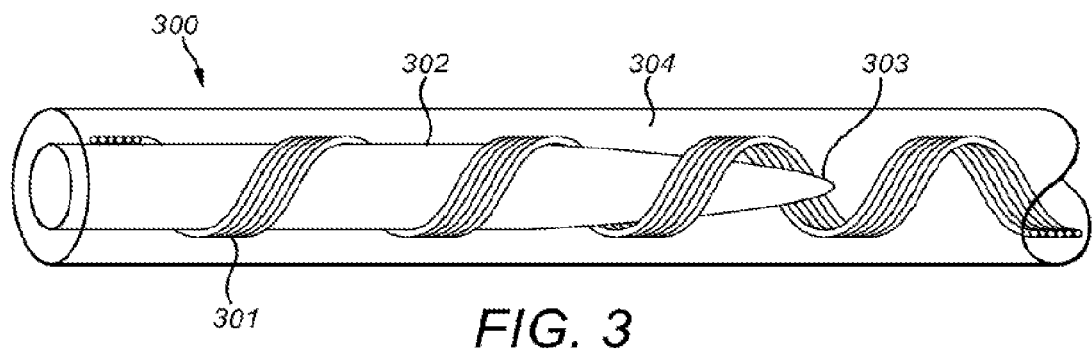
FIG. 3 shows an embodiment of the present invention having a conical lead core.

FIG. 3 shows one embodiment where an electric lead 300 which has an lead carrier material 304 that contains parallel embedded lead wires 301. As shown in FIG. 3, the lead wires 301 are wound in an elongated helix about a central longitudinal axis of the electrode lead 300. The embedded lead wires 301 may also be arranged in other suitable forms than in an elongated helix. For example, the lead wires 301 may be shaped in a substantially sinusoidal form about a central longitudinal axis of the electric lead 300.

A conical lead core 302 is fixed and enclosed in the lead carrier 304 within the wire helix for providing impact strain relief to the lead wires 301 by resisting radial and/or axial deformation from external impact force. The lead core 302 may be made of a flexible polymer material that may have an elastic module value and/or a shore-A hardness value greater than some given threshold value. For example, the lead carrier 304 material may be silicone of medium shore-A hardness (e.g. NUSIL MED-4244 or Applied Silicone LSR40), while the lead core 302 material may have a higher shore-A hardness (e.g. NUSIL MED-4770).

In other specific embodiments, the lead core 302 may be made of a flexible metallic material, for example, a shape memory alloy (SMA) such as Nitinol. The flexible metallic material may be a single wire having a thickness e.g. between 0.4 mm and 0.1 mm, or more preferably between 0.3 mm and 0.2 mm. Or the lead core 304 may be formed from bundled fibers or wires which may run in parallel or be braided. Lead core fibers may be made of inorganic materials such as carbon basalt (e.g. CBF—continuous basalt fibers) or glass, or from organic materials such as polypropylene, polyethylene, polyamide, aramid, spun liquid crystal polymer (e.g. Vectran) or other materials from these groups. Alternatively, they may be made from shape memory alloy such as Nitinol, e.g. having a bundle thickness between 0.4 mm and 0.1 mm, or more preferably between 0.3 mm and 0.2 mm. The material of the lead core 302 resists elongation of the electric lead 300 in case of a mechanical impact and also restricts diametric compression of the electric lead 300.

Whatever the specific choice of the material of the lead core 302, the flexibility of the electric lead 300 should be preserved. It is important that the surgeon can be able to bend the electric lead 300 to properly implant it, for example, to insert the electric lead 300 through the holed drilled into the skull bone, preferably as easily as without this core element 302 being present.

To satisfy the competing requirements of mechanical strength and impact resistance versus high flexibility suggests that it is important to choose an intelligent set of ratios between the radii of the various elements of the electric lead 300. For example, the ratio between the lead core 302 radius ($r_C$) and the electric lead 300 radius ($r_L$) may be selected to be greater than 0.1 and less than 0.7: $0.1 < r_C/r_L < 0.7$. In a preferred embodiment this ratio maybe between $0.33 < r_C/r_L < 0.66$. In addition, the ratio between the radius of the helical shape of the lead wires 301 ($r_H$) and the lead core 302 radius ($r_C$) should be selected to be between 1+x and 1.5, where x is the ratio between the radius of the lead wires 301 themselves (including isolation) and the lead core 302 ($r_C$). (A ratio between the radii of the wire helix ($r_H$) and the core ($r_C$) represents the value of 1+x when the lead wires 301 are directly wound around the lead core 302). In a preferred embodiment, the ratio $r_H/r_C$ may be between 1+x and 1.3, or even more preferably between 1+x and 1.25.

The conical end 303 of the lead core 302 ensures that there is not an abrupt transition of mechanical lead properties between the impact-protected part of the electric lead 300 and the unprotected part. Where the lead core 302 is made of individual wires or fibers, each of these may extend by different amounts towards the conical end 303 to provide a smooth transition.

Figure 4:
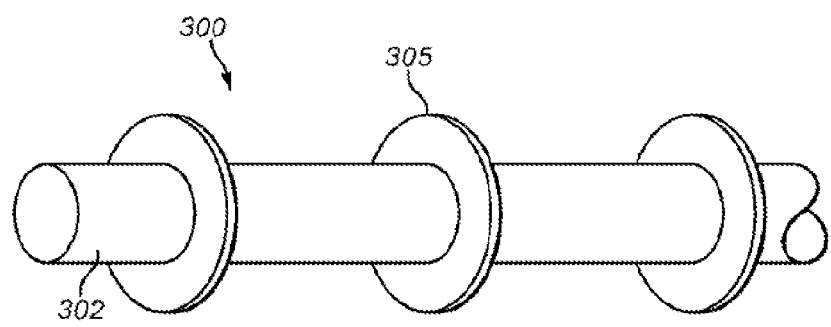
FIG. 4 shows an embodiment of the present invention having a rod-shaped lead core with support ribs.

FIG. 4 shows structural elements of an embodiment of a rod shaped lead core 302 with support ribs 305 that are perpendicular to the lead core 302 and distributed along the length of the lead core 302. The support ribs 305 help anchor the lead core 302 within the lead carrier 304 material and also help resist radial and/or axial deformation from external mechanical impacts on the electric lead 300.

In contrast to some previous schemes for temporarily using a stiffener element to assist with surgical insertion of the electrode, which is then removed, the lead core 302 element is securely fixed within the lead carrier 304 and remains as a structural element of the electric lead 300 after surgery to provide lasting post-surgical protection from external impacts. Moreover, proper design of the lead core 302 and the electric lead 300 should maintain full flexibility of the electric lead 300 rather than making it stiffer for surgical handling as with the prior art schemes. In addition, the prior art intra-surgical stiffener element is designed to be placed at the cochleostomy opening (or other location where the lead may be buckled during insertion), whereas the lead core 302 is placed close to the basal end of the electric lead 300 near the implant housing where it runs relatively unprotected after surgery on top of skull bone. It is also worth noting that the prior art surgical stiffener element does not describe how to deal with lead wires 301 that wound in an elongated helical shape embedded within an lead carrier 304 as here.

Figure 5:
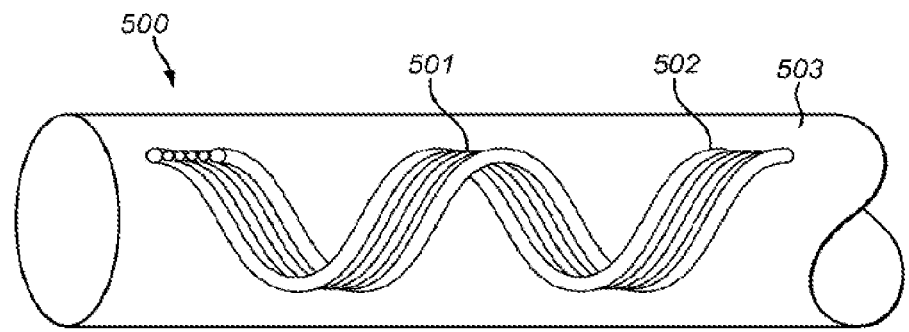
FIG. 5 shows an embodiment of the present invention with support wires along each outer edge of the helical wire ribbon.

Embodiments of the present invention also include other specific approaches for mechanically protecting the lead wires. FIG. 5 show an implantable electric lead arrangement for a medical implant system where an electric lead 500 has a lead carrier 503 which contains parallel embedded lead wires 501. As shown in FIG. 5, the lead wires 501 are wound in an elongated helix about a central longitudinal axis of the electric lead 500. The embedded lead wires 501 may also be arranged in other suitable forms than in an elongated helix, for example, the lead wires 501 may be shaped in a substantially sinusoidal form about a central longitudinal axis of the electric lead 500.

At least one support wire 502 is parallel to the lead wires 501 and has a higher strain energy absorption capacity than the lead wires 501 to mechanically strengthen the lead wires 501 against external impact force. In the specific embodiment shown in FIG. 5, there are multiple support wires 502, one along each outer side of the helical ribbon of lead wires 501. The at least one support wire 502 and the lead wires 501 of the helical ribbon may form a single integrated structural element, or they may be structurally separate elements wound together in a helical ribbon. In order to absorb the tensile forces acting on the lead wires 501 in the case of a mechanical impact onto the electric lead 500, the support wires 502 may be thicker and/or may be made of a different material (e.g. different metallic alloy, manufactured fiber or polymer) than the lead wires 501.

Figure 6:
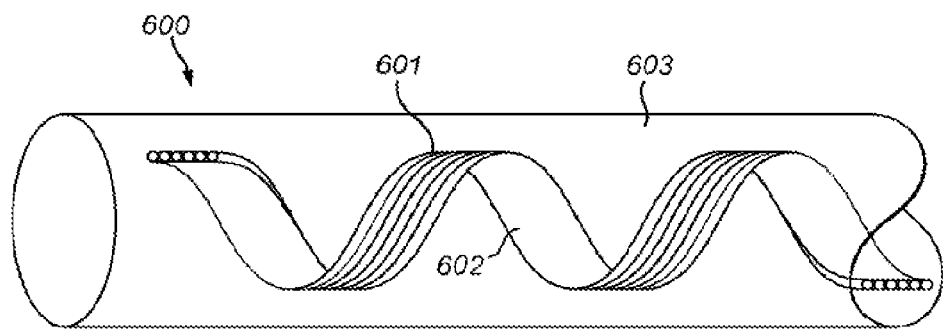
FIG. 6 shows an embodiment of the present invention with a support substrate beneath the helical wire ribbon.

Embodiments of the present invention also include an implantable electric lead arrangement for a medical implant system such as the one shown in FIG. 6. An electric lead 600 has a lead carrier 603 that contains parallel embedded lead wires 601. As shown in FIG. 6, the lead wires 601 are wound in an elongated helix about a central longitudinal axis of the electric lead 600. The embedded lead wires 601 may also be arranged in other suitable forms than in an elongated helix, for example, the lead wires 601 may be shaped in a substantially sinusoidal form about a central longitudinal axis of the electric lead 600.

A impact protection ribbon 602 lies in a plane beneath the lead wires 601 acting as a wire support substrate that mechanically supports the lead wires 601 and protects the lead wires 601 from external impact force. The lead wires 601 and the impact protection ribbon 602 are wound together in an elongated helical ribbon about a central longitudinal axis of the electric lead 600. The impact protection ribbon 602 may be made of thermoplastic material, fluorinated ethylene propylene (FEP), polyethylene or poly-etheretherketone (PEEK) material, which may be molded around the lead wires 601 or glued to the lead wires 601 to form a wire support substrate.

In some embodiments, the impact protection ribbon 602 may not be fixed connected to the lead wires and thus does not act as a wire support substrate. Rather, the impact protection ribbon 602 may be wound coaxially but separately with the lead wires 601 in an elongated helical ribbon about a central longitudinal axis of the electric lead 600 and mechanically protects the lead wires 601 from external impact force. In such embodiments, the impact protection ribbon 602 may be coaxially outside or coaxially inside the lead wires 601 and may be made of fluorinated ethylene propylene (FEP), polyethylene, poly-etheretherketone (PEEK) material or superelastic Nitinol material.

Figure 7:
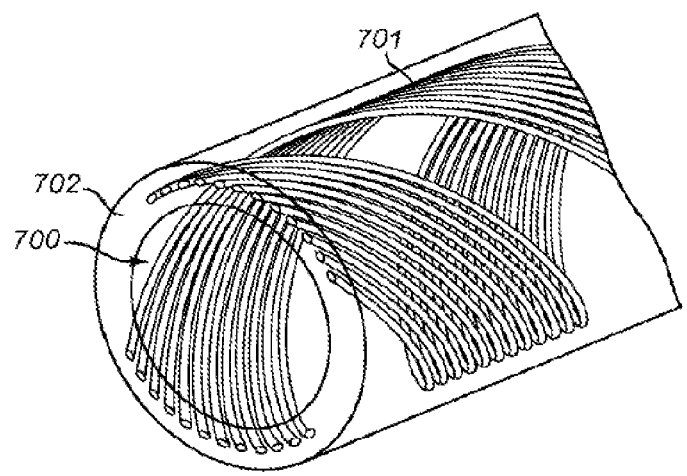
FIG. 7 shows an embodiment of the present invention having a hollow lead core.

FIG. 7 shows an embodiment similar to that of FIG. 3 but without a hollow core element 700. The lead wires 701 are wound in an elongated helix about a central longitudinal axis of the electric lead and embedded in a hollow cylinder of core material 702. The embedded lead wires 701 may also be arranged in other suitable forms than in an elongated helix, for example, the lead wires 701 may be embedded in core material 702 and shaped in a substantially sinusoidal form about a central longitudinal axis of the electric lead. A hollow lead core 700 reduces the overall volume of silicone in the electric lead and so reduces the amount of silicone displaced in a longitudinal direction during an impact. As a result the longitudinal pulling forces on the lead wires 701 during an impact are reduced, leading to better impact resistance. FIG. 7 shows the approximate relative proportions of a hollow core for an implant electrode. The ratio of hollow core to electrode lead diameter should be about the same as proposed above.

Embodiments of the present invention such as those described above provide protection of an implantable electric lead against mechanical impact with lower risk of lead wire breakage in case of such mechanical impacts. And despite the increased robustness of the electric lead against a mechanical impact, the elasticity and flexibility of the electric lead are less electric lead. Depending on the specific core material used, the electric lead can be elastic (to flip back after being bent), malleable (to retain the new shape when bent), or floppy. Although additional components and manufacturing steps are needed in comparison to an unprotected electric lead, the still uncomplicated electrode structures allow for easy manufacturing processes.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electric lead arrangement for a medical implant system, the arrangement comprising:
   an implantable electric lead containing a plurality of parallel lead wires wound in an elongated helix about a central longitudinal axis; and
   a conical shape lead core fixed and enclosed within the wire helix for providing impact strain relief to the electric lead by resisting radial and/or axial deformation from external impact force;
   wherein the conical shape of the lead core is configured for a smooth transition between a lead core portion of the electric lead that is protected against external impact force, and a non-lead core portion of the electric lead that is unprotected from external impact force.

2. The implantable electric lead arrangement according to claim 1, wherein the lead core is made of a flexible polymer material.

3. The implantable electric lead arrangement according to claim 2, wherein the polymer material has an elastic module value greater than some given threshold value.

4. The implantable electric lead arrangement according to claim 2, wherein the polymer material has a shore-A hardness value greater than some given threshold value.

5. The implantable electric lead arrangement according to claim 1, wherein the lead core is made of a flexible metallic material.

6. The implantable electric lead arrangement according to claim 1, further comprising:
   a plurality of support ribs perpendicular to the lead core and distributed along the length of the lead core.

7. The implantable electric lead arrangement according to claim 1, wherein a base end of the lead core has a diameter less than 0.7 times the diameter of the electric lead.

8. The implantable electric lead arrangement according to claim 1, wherein the electric lead is a cochlear implant electrode lead connected at one end to an implantable cochlear implant processor and connected at another end to an intracochlear electrode array.

* * * * *